United States Patent
Contolini et al.

(10) Patent No.: US 9,549,717 B2
(45) Date of Patent: Jan. 24, 2017

(54) WIRELESS COMMAND MICROPHONE MANAGEMENT FOR VOICE CONTROLLED SURGICAL SYSTEM

(75) Inventors: Matteo Contolini, Santa Barbara, CA (US); Ted Applebaum, Santa Barbara, CA (US); Sankaran Panchapagesan, Goleta, CA (US)

(73) Assignee: Storz Endoskop Produktions GmbH, Tuttlingen (DE)

( * ) Notice: Subject to any disclaimer, the term of this patent is extended or adjusted under 35 U.S.C. 154(b) by 1811 days.

(21) Appl. No.: 12/560,661

(22) Filed: Sep. 16, 2009

(65) Prior Publication Data
US 2011/0063429 A1    Mar. 17, 2011

(51) Int. Cl.
*H04N 7/18* (2006.01)
*A61B 17/00* (2006.01)
*G10L 15/22* (2006.01)

(52) U.S. Cl.
CPC ........... *A61B 17/00* (2013.01); *G10L 15/22* (2013.01); *A61B 2017/00203* (2013.01); *G10L 2015/223* (2013.01)

(58) Field of Classification Search
CPC . A61B 1/0411; A61B 1/00036; A61B 1/0005; A61B 19/52
USPC .................................. 348/65–80; 600/20–50
See application file for complete search history.

(56) References Cited

U.S. PATENT DOCUMENTS

| | | | |
|---|---|---|---|
| 5,561,737 A | 10/1996 | Bowen | |
| 6,063,095 A | 5/2000 | Wang et al. | |
| 6,096,025 A * | 8/2000 | Borders | 606/1 |
| 6,219,645 B1 | 4/2001 | Byers | |
| 6,405,165 B1 * | 6/2002 | Blum et al. | 704/235 |
| 6,850,794 B2 * | 2/2005 | Shahidi | 600/427 |
| 6,959,260 B2 | 10/2005 | Rodman et al. | |
| 7,171,329 B2 | 1/2007 | Rodman et al. | |
| 7,283,423 B2 | 10/2007 | Holm | |
| 7,336,563 B2 | 2/2008 | Holm | |
| 7,352,652 B2 | 4/2008 | Holm et al. | |
| 7,362,656 B2 | 4/2008 | Holm | |
| 2002/0101918 A1 | 8/2002 | Rodman et al. | |

(Continued)

FOREIGN PATENT DOCUMENTS

| | | |
|---|---|---|
| EP | 1421913 A | 5/2004 |
| JP | 2002125983 A | 5/2002 |

(Continued)

OTHER PUBLICATIONS

Togt, et al.; "Electromagnetic Interference From Radio Frequency Identification Inducing Potentially Hazardous Incidents in Critical Care Medical Equipment"; Journal of American Medical Association (JAMA); Jun. 25, 2008; 7 pages.

(Continued)

*Primary Examiner* — Andy Rao
(74) *Attorney, Agent, or Firm* — Whitmyer IP Group LLC (57) ABSTRACT

A voice controlled surgical system including a wireless command microphone receiving audio input, a voice control module for generating commands from the audio input received by said wireless command microphone, a detection module for generating signals indicative of a proximity of said wireless command microphone, a switch module for disabling the commands in response to one or more of the signals, and an alarm module activated in response to the one or more of the signals.

12 Claims, 9 Drawing Sheets

(56) References Cited

U.S. PATENT DOCUMENTS

| | | |
|---|---|---|
| 2003/0182132 A1 | 9/2003 | Niemoeller |
| 2008/0049555 A1 | 2/2008 | Holm et al. |
| 2008/0281301 A1* | 11/2008 | DeBoer et al. .................. 606/1 |
| 2009/0076827 A1 | 3/2009 | Bulitta et al. |
| 2009/0175464 A1* | 7/2009 | Somen et al. ................. 381/74 |

FOREIGN PATENT DOCUMENTS

| | | | |
|---|---|---|---|
| JP | 2007175229 A | 7/2007 | |
| WO | 02089115 A1 | 11/2002 | |

OTHER PUBLICATIONS

Infra-Com ltd.; "Application Note: IrGT801A Chipset Wireless Audio Link based on Diffused Infrared Technology"; www.infra-com.com; Jan. 17, 2007; 15 pages.

European Search Report; Application No. EP 10 17 7219; Jan. 18, 2011; 6 pages.

Arthur C. Graesser, et al.: "Intelligent Tutoring Systems with Conversational Dialogue." AI Magazine, Winter 2001, vol. 22, No. 4, pp. 39-51.

OnLineMathLearning.com, ACT College Test, Oct. 19, 2012, pp. 1-3. <http://web.archive.org/web/20070701101411/http://www.onlinemathlearning.com/act-test>.

\* cited by examiner

WIRELESS COMMAND MICROPHONE MANAGEMENT FOR VOICE CONTROLLED SURGICAL SYSTEM

FIELD OF THE INVENTION

The invention relates to a voice controlled surgical system, and more specifically to a voice controlled surgical system including a means to manage wireless command microphones.

BACKGROUND OF THE INVENTION

Voice input is used in the operating room environment for tasks such as voice annotation, communication (e.g., telephone, video conference, etc.) and voice control. Some voice controlled systems include one or more command microphones worn by surgeons or other surgical staff, and connected to the surgical system via wire. Wired command microphones, requiring that the user be tethered to the surgical system, have drawbacks including restricting the surgeons' freedom of movement within the operating room ("OR").

Wireless command microphones allow surgeons to freely move about the OR. However, the use of a wireless command microphone raises safety concerns. For example, wireless command microphones allow a user the freedom to walk out of the OR and even into another OR without removing the command microphone. Thus, a surgeon may issue voice commands without realizing that he/she is controlling equipment in a different OR. Interference/cross-talk with other wireless communications systems may arise, and the radio link can be lost or broken. Finally, the battery on a wireless command microphone transmitter can run out.

There is a need in the art to address the problem of the user inadvertently issuing voice commands without realizing that he/she will be controlling equipment in a different OR. This problem is potentially dangerous for both the patient and surgical team (e.g., a surgical table starts moving inadvertently while a patient is being placed on it). There is also a need to detect and warn users when a wireless command microphone loses its data link or battery power to ensure that all intended voice commands are received and implemented.

Some systems are known to discontinue data communications when certain devices are no longer co-located in a particular room (e.g., U.S. Pat. No. 6,959,260 to Rodman et al.), however these prior art systems are not adapted for voice controlled surgical systems and do not warn users when a device is no longer co-located and do not address malfunctions such as a lost communication link or dead battery. Thus, there is a desire in the art to detect and inform the user and/or other staff via open room audible alarm and/or graphical representation, of any microphone malfunction (e.g., out of range, lost communication link, or dead battery), so that the user and/or OR staff, will not waste time trying to issue voice commands—for example in an emergency situation—and instead control the device(s) directly through their control panel or other available means.

SUMMARY OF THE INVENTION

It is an object of the present invention to solve the problem of surgeons inadvertently issuing voice commands via wireless microphones outside the OR.

Another objective is to provide a surgical system that can warn the user and/or OR staff when the wireless communication link between the command microphone and the surgical system is not working; caused by a dead battery, lost wireless communication link, or the like.

These and other objectives are achieved by providing a voice controlled surgical system which disables voice control when the user wearing the command microphone is not in the OR, by one or more passive or active detecting means and alerts the user when voice control is disabled. Voice control systems typically include an audio channel receiving audio input including a user's speech, a speech recognition module that converts the user's speech into a digital representation and a voice control module that validates and interprets the digital representation and issues corresponding commands suitable for control of intended devices and/or systems. Disabling voice control may be achieved by interrupting the functionality of the audio channel, speech recognition module, and/or voice control module. For example, the audio channel may be disabled by shutting down the wireless command microphone or a transmitter associated with the wireless command microphone, and/or by disabling a sound card associated with the wireless command microphone and/or transmitter. Additionally, disabling voice control may be achieved by interrupting functionality of the speech recognition module and/or the voice control module, thus preventing commands from being sent to the intended devices and/or systems.

In one exemplary embodiment, a voice controlled surgical system is provided including a wireless command microphone receiving audio input, a voice control module for generating commands from the audio input received by the wireless command microphone, a detection module for generating signals indicative of a proximity of the wireless command microphone, a switch module for disabling the commands in response to one or more of the signals, and an alarm module activated in response to the one or more of the signals. In some embodiments, the detection module generates a first signal when the wireless command microphone is outside of a particular room, a second signal when the wireless command microphone is inside the particular room, and a third signal in response to at least one of a power and communication loss with the wireless command microphone.

In one embodiment, the system further includes at least one video camera recording video images of an operating room and an image recognition module, in communication with the detection module, receiving the video images and generating a signal indicative of the wireless command microphone being present in the operating room if the wireless command microphone is identified in the video images. The wireless command microphone may further include at least one visual feature uniquely identifying the wireless command microphone.

Objects of the present invention are further achieved by provision of a voice controlled surgical system including an emitter producing an ultrasound signal, a wireless command microphone receiving at least one of a speech input and the ultrasound signal, a detection module detecting the receipt of at least one of the speech input and the ultrasound signal, a voice control module for generating commands identified in the speech input, and a switch responsive to the detection module for controlling at least one of the wireless command microphone and the voice control module, wherein the switch enables the commands in accordance with the detection of the ultrasound signal.

In some embodiments, a lost communication link or dead battery is identified by both a missing ultrasound signal from the wireless command microphone output, and a flat or absent audio signal (or specific signal generated at the receiver to indicate the particular status). The wireless command microphone being out of the room may be identified when the ultrasound signal is missing from the wireless command microphone output, and there is no audio signal (e.g., some background noise is still being detected in the wireless command microphone output).

Further provided is a voice controlled surgical system including a computer including a voice control module, a wireless command microphone in wireless communication with the computer, a reference microphone having a fixed location, a detection module for comparing a first audio input received by the wireless command microphone and a second audio input received by the reference microphone, a switch responsive to the detection module for disabling voice commands if the first audio input received by the wireless command microphone and the second audio input received by the reference microphone are substantially different, and an alarm responsive to the detection module and activated when the audio input received by the wireless command microphone and the audio input received by the reference microphone are substantially different.

In some embodiments, a lost wireless communication link or dead battery is identified when there is a flat signal (or specific signal generated at the wireless receiver to indicate the particular status). Alternatively (or in conjunction), speaker identification modules operate on the signals from the reference and wireless command microphone. When the wireless command microphone is operating correctly (e.g., good battery, good communication link) both identification modules identify the current user and agree on his/her identity. If wireless communication is interrupted (e.g., dead battery or lost communication link), the user will still be identified on the reference microphone, but not on the wireless command microphone indicating a problem with wireless communication.

The present invention allows the users of the system to enjoy the benefits of a wireless microphone such as added mobility, better audio quality via improved communication technologies, more effective voice control, while at the same time reducing the operational risks associated with a wireless microphone; such as, control of wrong devices, dead battery, lost wireless communication link, and the like.

Other objects of the invention and its particular features and advantages will become more apparent from consideration of the following drawings and accompanying detailed description.

DETAILED DESCRIPTION OF THE INVENTION

Figure 1A:
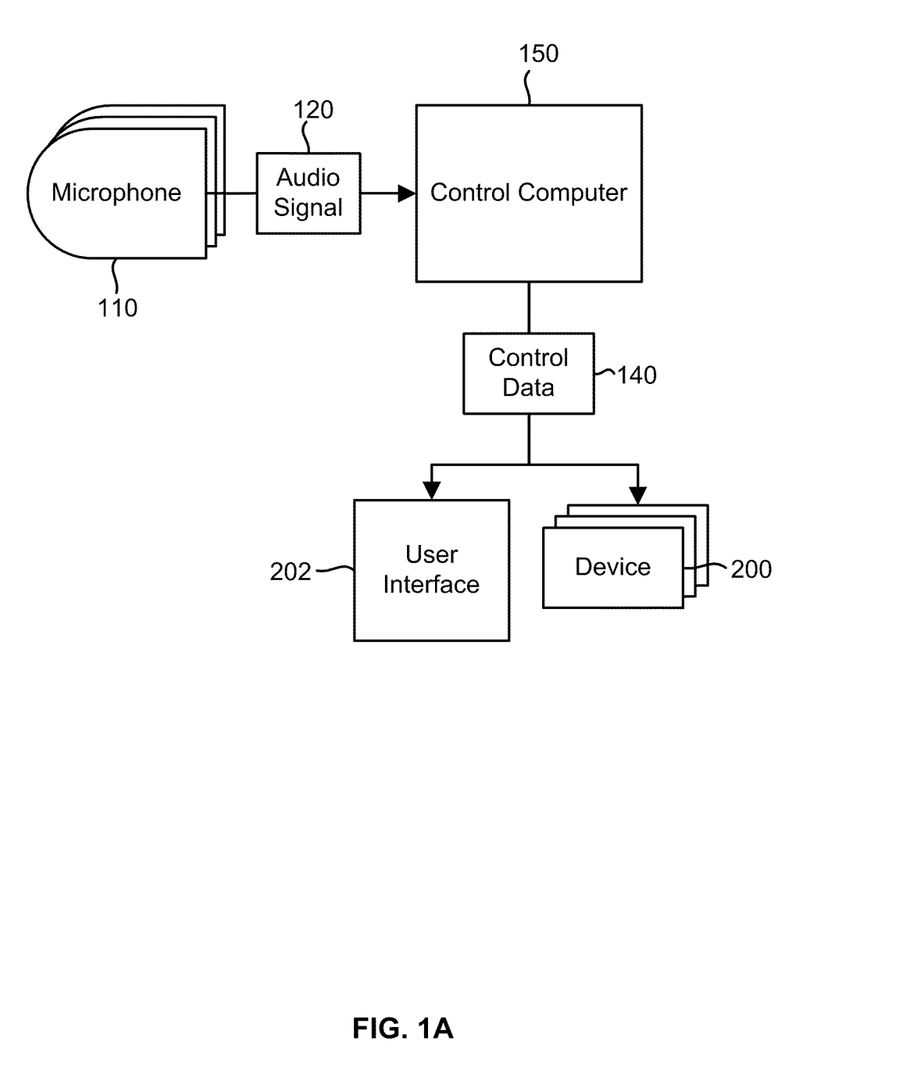
FIGS. 1A-1B illustrate a system according to an exemplary embodiment of the present invention.

FIG. 1A illustrates a voice controlled surgical system according to an exemplary embodiment of the present invention. The system includes a control computer 150 and one or more microphones 110, at least one of which is a wireless command microphone. The wireless command microphone is a portable device, worn or carried by a user, such that the user's speech may be transduced at high signal-to-noise ratio, due to the close proximity to the user's mouth. The wireless command microphone may include a number of components such as the microphone, transmitter, and battery.

The microphones 110 receive audio input including user's speech. Audio signals 120 are received by the computer 150 from the microphones 110. The control computer 150 includes one or more software modules or components for processing the audio input and controlling devices in communication with the system. The control computer 150 may include a speech recognition module that converts the user's speech into a digital representation and a voice control module that validates and interprets the digital representation and issues corresponding commands suitable for control of intended devices and/or systems.

When one of the wireless command microphones 110 is outside of a particular range or not in the proximity of the surgical system (e.g., outside of the OR), or the wireless command microphone malfunctions or loses power, the system is adapted to disable voice control from that wireless command microphone by one or more passive or active microphone management means.

If at least one wireless command microphone 110 is in a desired range or proximity, e.g., in the OR, that wireless command microphone 110 and/or a voice control module of the computer 150 remain operable. If the at least one wireless command microphone 110 is determined to be outside the desired proximity and/or a malfunction or power loss occurs, voice control for that wireless command microphone is disabled. For example, the audio channel may be disabled by shutting down the wireless command microphone or a transmitter associated with the wireless command microphone, by disabling a sound card associated with the wireless command microphone and/or transmitter. Additionally, disabling voice control may be achieved by interrupting functionality of the speech recognition module and/or the voice control module, thus preventing commands from being sent to the intended devices and/or systems.

The present invention may be used to detect a wireless command microphone 110 being outside a desired range or proximity (e.g., outside of the OR) and also a power loss or malfunction of a wireless command microphone 110, such as a dead battery. For example, the voice control system may identify whether a wireless command microphone 110 is either out of the room, a wireless command microphone battery is dead, or a wireless communication link has been lost. The voice control system is adapted to specifically identify when a wireless command microphone 110 is out of the OR; and, in some embodiments, depending on the features supported by the wireless communication system, may distinguish between a dead battery and the wireless communication link being lost. The present invention may also enable more than one wireless command microphone(s)

110; and disable a particular wireless command microphone 110 in accordance with one or more passive or active microphone management means.

In some embodiments, a range limitation is imposed on the wireless command microphone 110. A wireless communication system, which only works within a short distance of the surgical system, may be used. For example, the power of a transmitter associated with the wireless command microphone 110 is limited to reduce the range of the wireless communication system to the size of the particular operating room in which it is to be employed (e.g., within a radius commensurate with the desired area of control).

In other embodiments, the wireless command microphone 110 communicates audio signals 120 with the computer 150 via a diffuse infrared ("IR") channel. Diffuse (non-line-of-sight) IR ensures that voice commands are only accepted from within the operating room by using a transmission means which will not pass through walls. A diffuse IR transmission means has sufficient bandwidth to support high-quality voice transmission. Diffuse IR typically floods a room with an infrared signal, and relies on reflections from ceiling, walls, floor, and other surfaces to maintain robust non-directional communication within the room.

Figure 1B:
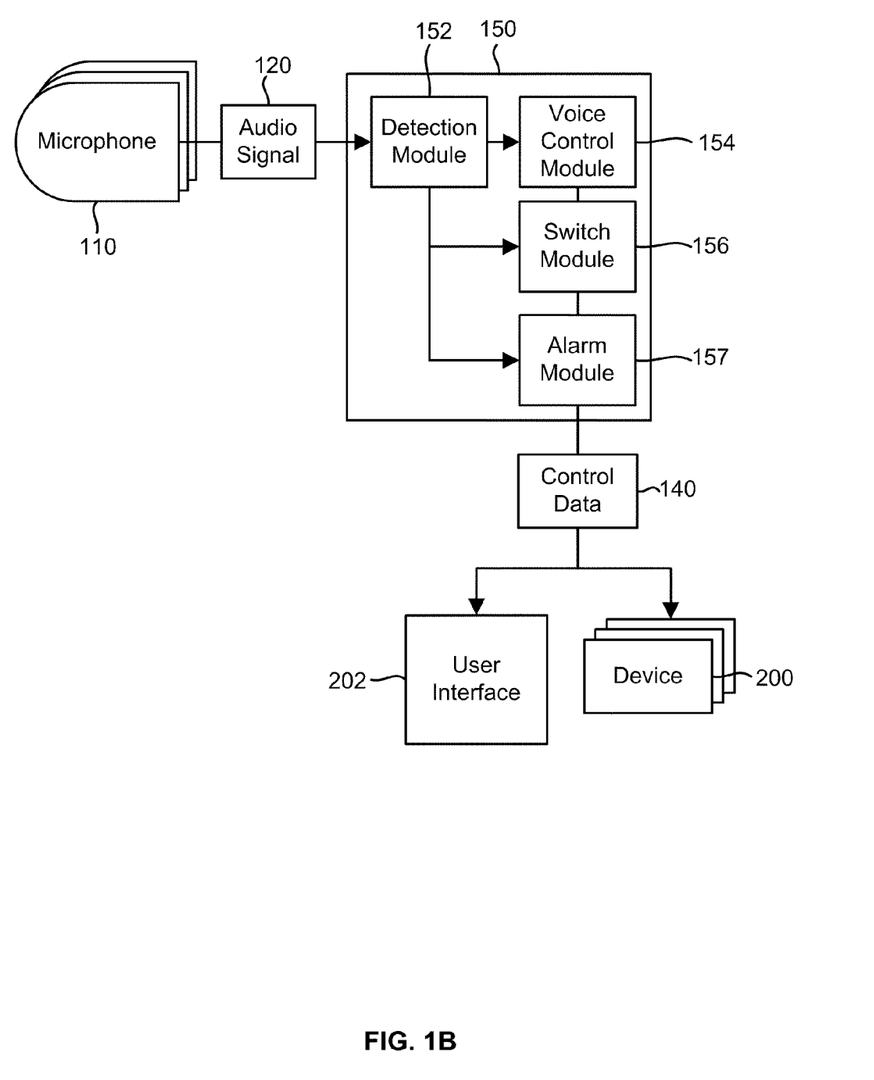

FIG. 1B illustrates a voice controlled surgical system according to an exemplary embodiment of the present invention employing one or more active solutions. The voice controlled surgical system includes a detection module 152 for detecting the presence, range, and/or proximity of at least one of the command microphones 110. In some embodiments, the detection module 152 includes or is in communication with an image recognition module. The system may also include a speech recognition module (not shown) that converts the user's speech into a digital representation.

The surgical system includes a voice control module 154 for controlling one or more devices 200 of the system based on speech commands derived from the audio signals 120. If a wireless command microphone 110 is determined to be in a desired range or proximity, e.g., in a particular OR, and is functioning correctly; then voice control remains enabled. If the command microphone 110 is determined to be outside the desired proximity, malfunctioning and/or experiencing a power loss; then voice control is disabled, e.g., by a switch or switch module 156. For example, the detection module 152 may generate a first signal indicative of the command microphone 110 being outside the desired proximity. In some embodiments, the detection module 152 may generate a second signal indicative of the wireless command microphone being within the desired proximity. If the command microphone 110 is determined to be outside the desired proximity, malfunctioning and/or experiencing a power loss; the system may further activate an alarm module 157 to warn the user with an audible or visual alarm.

Figure 2:
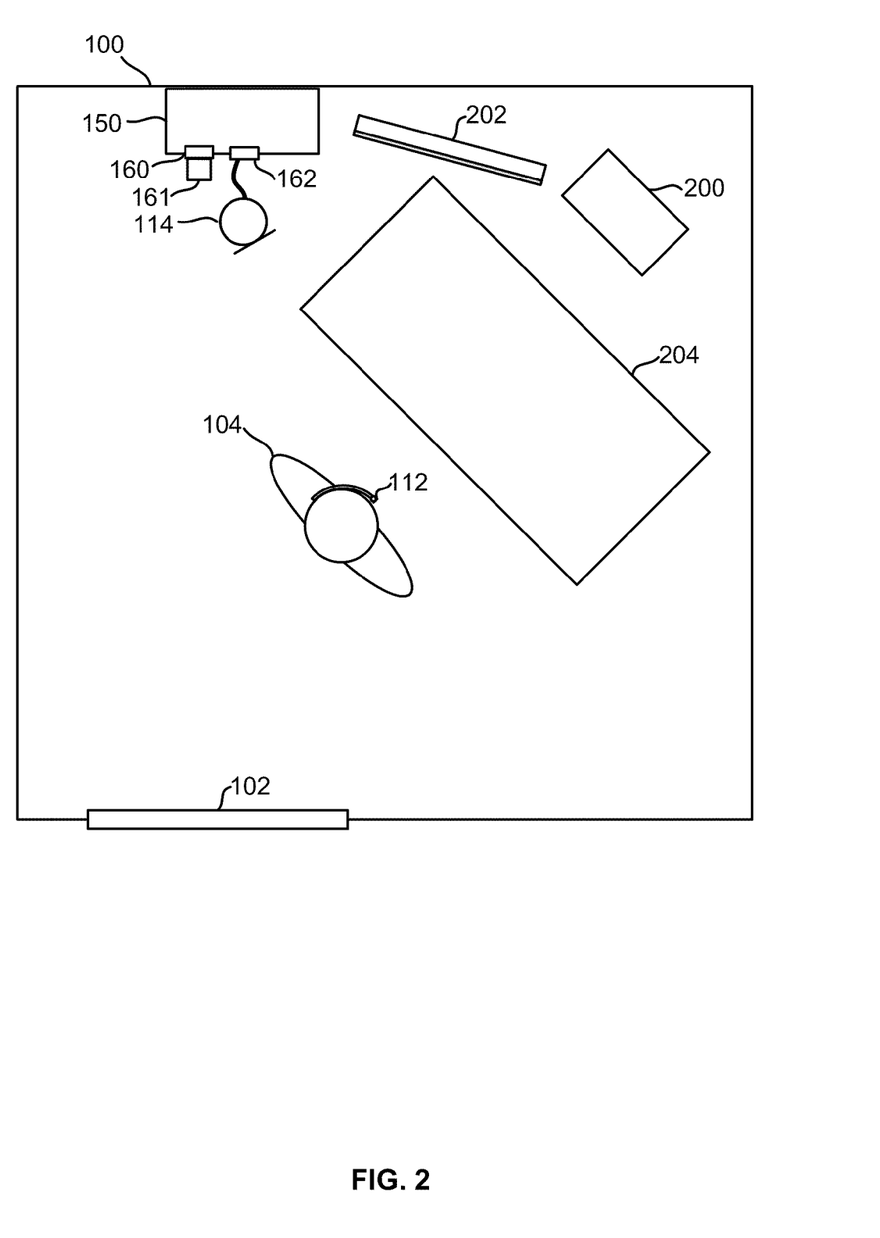
FIG. 2 is a top view of an operating room including a system according to an exemplary embodiment of the present invention.

FIG. 2 illustrates an operating room 100 including the voice controlled surgical system of FIG. 1, in which the detection module 152 employs a cross-correlation analysis with a reference microphone ("CCRM"). Utilizing CCRM, an audio signal, such as that received at the detection module 152 from a wireless command microphone, is compared with an audio signal received from at least one fixed position reference microphone. If the reference microphone audio signal is adequately similar to the wireless command microphone audio signal, it can be inferred that the wireless command microphone, and thus the user, is in the OR 100. If the audio signals adequately differ, including a difference in time (i.e., the reference microphone audio signal lags the wireless command microphone audio signal), then the wireless command microphone, and thus the user, is too far away from the reference microphone, and/or is outside of the OR 100.

The exemplary voice controlled surgical system includes at least one wireless command microphone 112 worn by a user 104 (e.g., surgeon) in the OR 100. The voice controlled surgical system may further include the control computer 150. The wireless command microphone 112 is wirelessly connected to the computer 150 via a wireless receiver 161 and sound card 160. The wireless command microphone 112 communicating with the computer 150 comprises at least one first communication channel.

In the present embodiment, the system includes one or more reference microphones 114 at generally fixed locations in the OR 100. For example, the system may include an omni-directional reference microphone 114 (e.g., wired microphone) mounted on a tripod next to one of the walls of the OR 100, e.g., at a height of about 2 meters and pointing toward the center of the OR 100. The reference microphone 114 may alternatively be mounted on a light, boom arm, or the surgical table 204. The reference microphone 114 is connected to a sound card 162 (e.g., USB soundcard) of the control computer 150. The reference microphone 114 communicating with the computer 150 comprises at least one second communication channel.

The OR 100 may include any number of devices 200 controlled by the surgical system including, e.g., user interfaces and/or monitors 202, a surgical table 204, endoscopic cameras, alarm(s), insufflators, light sources, media control modules, an Advanced Image and Data Archiving System ("AIDA"), etc. Speech received via the first communication channel may be used for speech recognition input, e.g., for controlling the devices 200 within the OR 100. Sound received via the second communication channel may be used to perform a cross-correlation analysis with the sound received by the first communication channel (e.g., user speech). Voice control is disabled if the cross-correlation between the signal at the first communication channel and the signal at the second communication channel is not sufficiently high. In some embodiments, speech recognition results are accepted as commands when the microphone 112 re-enters the OR 100. In other embodiments, voice control must be explicitly reactivated.

The cross-correlation analysis may be performed in the time-domain, frequency-domain or in the domain of other parameters extracted from the signals (e.g., cepstral coefficients). In one exemplary embodiment, the comparison of the two audio signals is performed by calculating their cross-correlation, defined as:

$$(s*r)(x) = \int s^*(t) r(t+x) dt,$$

where s(t) and r(t) are the audio signals and s*(t) indicates the complex conjugate of s(t). When dealing with discrete, real signals, the generic definition of cross-correlation becomes:

$$(s*r)[j] = \sum_n s[n] r[n+j].$$

In one exemplary embodiment, the cross-correlation is calculated in the detection module 152 from signals in the mel filter cepstral coefficient ("MFCC") domain. The computational gain is clear since time domain signals are sampled at 16 kHz, while the MFCC features consist of 13-dimensional vectors at a rate of 100 Hz. Another advantage of using MFCC features is that they are more immune to background noise.

A further computational gain is obtained by limiting the maximum time lag in the cross-correlation computation (the j index in the second formula above). Peaks in the cross-correlation function over different lag values j are identified, where the lag value allows for accounting for the different distance that the audio signal has to travel (e.g., 1-2 cm for the wireless headset vs. a few meters for the reference microphone). Since the time resolution of the MFCC features may be too small (10 ms) to capture sound travel delays within a radius of several meters—as in a typical OR—it may be sufficient to only consider values of 0 or 1 for the lag. In some embodiments, the lag is allowed to span a range from 0 to 5.

In the exemplary embodiment, the cross-correlation algorithm involves splitting the time-domain signals at the first communication channel, s(t), and at the second communication channel, r(t), into 1-second segments. For each segment i, MFCC features $\overline{S}_i(n)$ and $\overline{R}_i(n)$ are calculated, where n is the index of successive feature vectors (for a 1-second speech segment, 0≤n<100). The signal energy e(l) is also computed (note that l and n are independent indexes):

$$e(l) = \sum_{i=l-P}^{l+Q} [S(i)]^2$$

For each value of the time lag j, the cross-correlation $cc_i(j)$ is calculated as $$cc_i(j) = \sum_n \overline{S}_i(n) \cdot \overline{R}_i(n+j)$$

where · indicates the scalar product of the two vectors. The cross-correlation for segment i is taken as:

$$C(i) = \max_j cc_i(j).$$

The C(i) values are further smoothed as follows:

$$C'(i) = \sum_{k=-N}^{k=N} C(i+k)w(k)$$

where w(k) are the normalized 2N+1 coefficients of a triangular window, defined as:

$$w(k) = \frac{w'(k)}{\sum_k w'(k)},$$

and $$w'(k) = \begin{cases} \frac{N-k+1}{N+1}, & 0 \le k \le N \\ \frac{N+k+1}{N+1}, & -N \le k < 0 \end{cases}$$

The energy values e(l) are also smoothed to obtain their long-term average. This may be performed, for example, by means of a causal rectangular window:

$$E(l) = \frac{\sum_{m=l-M}^{m=l} e(m)}{M}, \text{ where } e(m) = 0 \text{ for } m < 0.$$

Typical values for the constants above are: N=10 and M=50. The decision variable d(l) is updated according to the rule:

$$d(l) = \begin{cases} 0, & l \le 0 \\ d(l-1), & e(l) < E(l) \\ 1, & (e(l) \ge E(l)) \text{ AND } (C'(i_l) \ge G) \\ -1, & (e(l) \ge E(l)) \text{ AND } (C'(i_l) < G) \end{cases}$$

where G is an empirical threshold and $i_l$ indicates the point in the series C'(i) which is closest to time l (note that the cross-correlation and the energy may be calculated at time intervals that are independent from each other). The wireless headset is assumed to be within the room when d(l)==1, and to be outside of the room when d(l)==−1. The initial state (d(l)==0) indicates that no decision has been made yet. The decision is only updated when the energy is above its long term average, since during silent segments the cross-correlation tends to be low, being only determined by background noise. The threshold G may be either fixed or adaptively estimated while the system is being used.

In another embodiment, the CCRM analysis may be performed in the detection module 152 from digitized signals in the time domain. In this case, since the typical signal sampling rate is 8 kHz or above, the lag factor can be used to measure—with higher resolution—the time it takes to the audio wave to travel from the position of the wireless microphone 112 (user) to the position(s) of the reference microphone(s) 114. The lag or travel time of the audio is identified as the value j corresponding to the maximum value of $cc_i(j)$, or identified by considering values j corresponding to several peaks of the cross-correlation function $cc_i(j)$. The lag can be translated into a distance (since the speed of sound is known), and thus used to more accurately determine the distance of the user from the reference microphone(s). For example, at a sampling rate of 16 kHz, a delay of 47 samples corresponds to approximately one meter, assuming the speed of sound to be 340 meters/sec. In this embodiment (CCRM analysis performed in the time domain), the value of the lag will be allowed to span a wider range, that can also be determined according to the size of the particular room where the system is meant to operate.

The time lag value j corresponding to the maximum value of $cc_i(j)$ may also be taken into consideration for determining the decision d(l), as high values of j indicate that the audio waveform had to travel a longer distance to reach the reference microphone, and thus that the wireless microphone is not in the proximity of at least one of the reference microphones. To improve the robustness of the decision, another value j' of the lag can be estimated by a different algorithm. For example, an adaptive filter may be used to estimate the impulse response between the audio signals recorded by the wireless and reference microphones. This adaptive filter may be based, for example, on the widely used Normalized Least Mean Square ("NLMS") algorithm.

The peak of the impulse response energy would correspond to the delay of the direct path of sound transmission from the talker to the reference microphones. As mentioned above, at a sampling rate of 16 kHz, the delay for each meter travelled by sound corresponds to approximately 47 samples. Hence, a FIR adaptive filter of length 512 to 1024 taps can measure wireless to reference microphone distances approximately between 10 m and 20 m, which would be sufficient for usual sizes of operating rooms. Therefore, the delay j' of the peak of the impulse response energy provides an independent estimate of the distance between the wireless and reference microphones.

In another embodiment, the decision d(l) is performed by a machine learning algorithm such as Neural Networks, Decision Trees, Linear Classifiers, etc., which provides an efficient way to combine all inputs (e(l), E(l), C'(i), j, j', etc.) for the decision (classification) process.

Figure 3A:
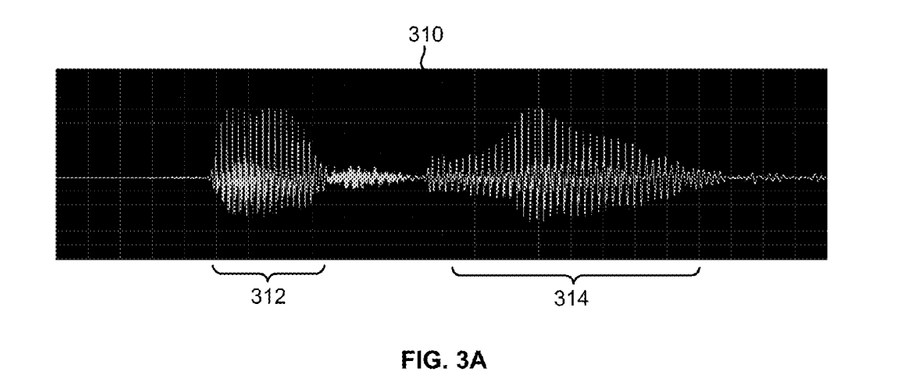
FIGS. 3A-3D illustrate waveforms recorded at microphones in the operating room shown in FIG. 2.
Figure 3B:
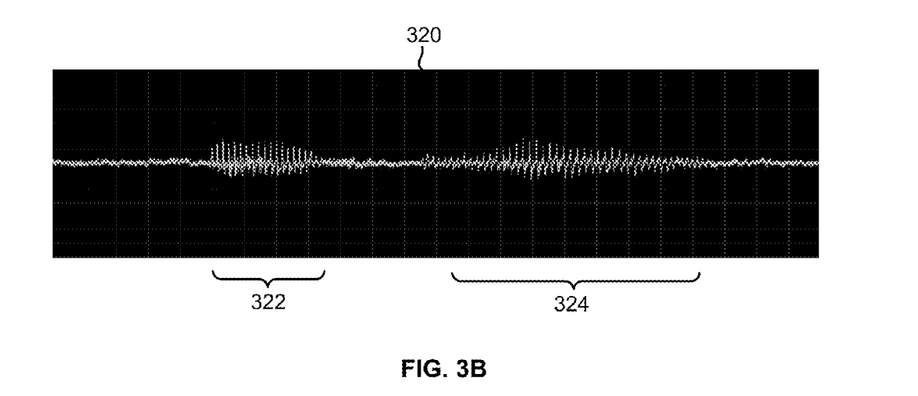

FIGS. 3A and 3B illustrate waveforms 310/320 recorded from the first communication channel and at the second communication channel, respectively, in the operating room shown in FIG. 2. The speech produced by the user 104 is picked up by the reference microphone 114. For example, the speech signal 312 in the waveform 310 is also found in the waveform 320 (see, e.g., 322) recorded at the reference microphone 114. Thus, while the signal at the reference microphone 114 includes some additional noise, the speech signal information is found in both waveforms.

Figure 3C:
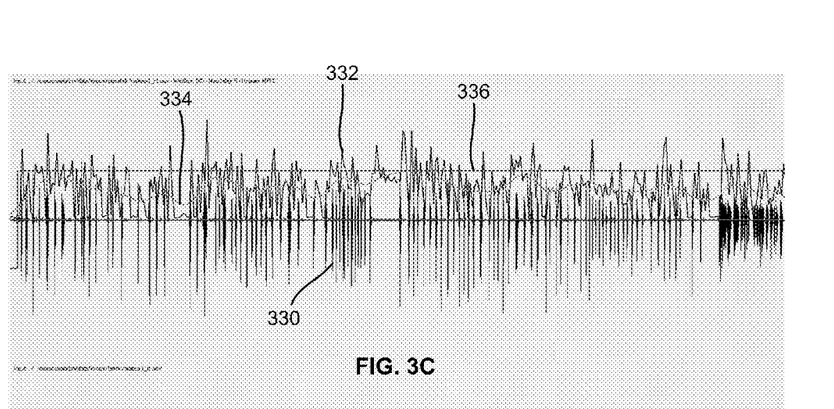
Figure 3D:
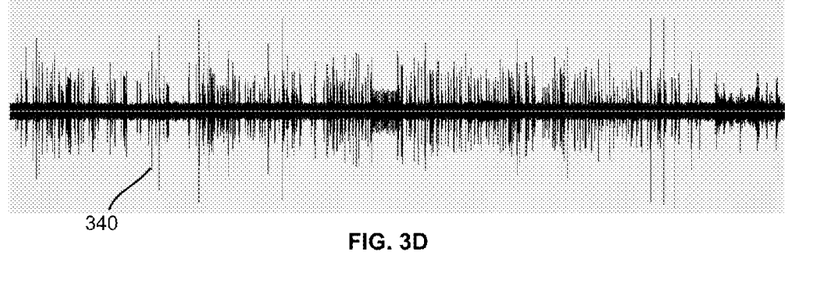

FIGS. 3C and 3D illustrate additional waveforms recorded from the wireless microphone 112 and reference microphone 114 in the OR 100 shown in FIG. 2, along with the cross-correlation determined by the above described methods. The speech signals are represented by the lines 330 and 340 for the wireless microphone 112 and reference microphone 114, respectively. The cross-correlation is represented by the line 332, the smoothed cross-correlation by the line 334, and the decision is represented by the line 336.

Figure 4:
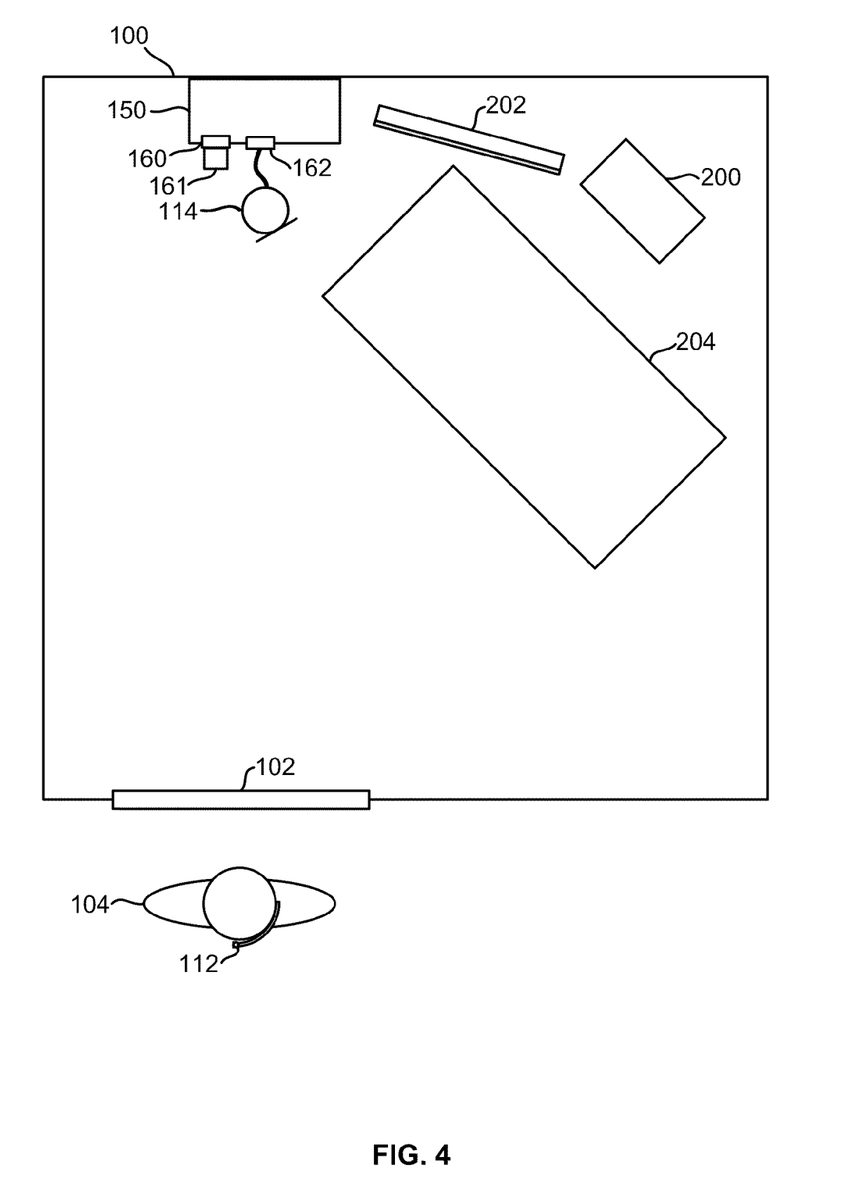
FIG. 4 is another top view of an operating room including a system according to an exemplary embodiment of the present invention.
Figure 5A:
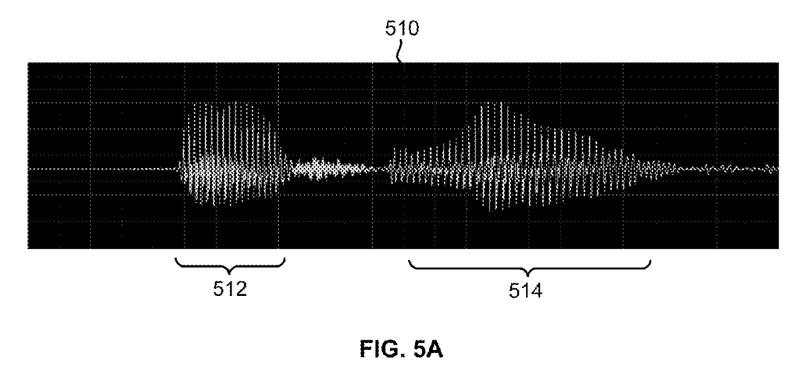
FIGS. 5A-5B illustrate waveforms recorded at microphones in the operating room shown in FIG. 4.
Figure 5B:
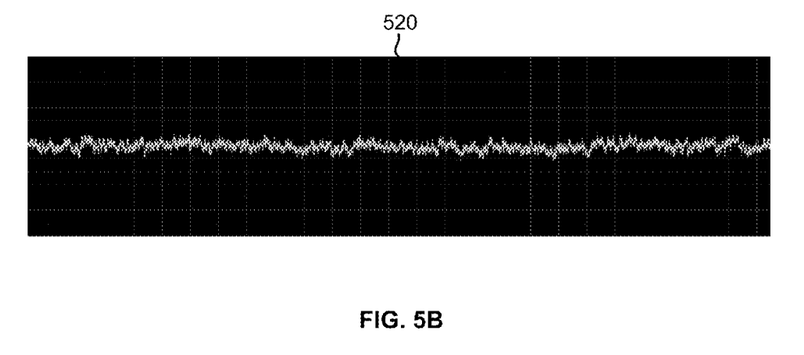

FIG. 4 is another top view of the operating room 100 including a system according to an exemplary embodiment of the present invention. In FIG. 4, the user 104 wearing the wireless microphone 112 is outside the OR 100 (e.g., through the door 102). FIGS. 5A and 5B illustrate waveforms 510/520 recorded at the wireless microphone 112 and the reference microphone 114, respectively, in the operating room shown in FIG. 4. In this case, the reference microphone 114 only records background noise with little in common with the signal at the wireless microphone 112. Thus, the speech signals 512/514 in the waveform 510 are not found in the reference waveform 520.

When it is determined that the wireless microphone 112 is outside of the OR 100, voice commands are prevented and/or not accepted. For example, the system may include a switch embodied in a software module 156 executing on the computer 150 and/or a hardware component on the computer 150 and/or wireless microphone 112. The switch may disable the voice control module 154 and/or the wireless microphone 112 (e.g., in response to a signal from the detection module 152). In some embodiments, the switch deactivates the sound card 160 or disables pairing between the wireless microphone 112 and the receiver 161. In other embodiments, the switch includes hardware attached to the microphone 112, or a "body-pack" thereof, with associated circuits to disable the microphone 112.

The system also provides a warning to user and/or OR staff when the wireless communication system is not working, e.g., either because the wireless microphone 112 is outside of the OR 100, a dead battery, and/or because of a lost communication link. For example, when it determined that the wireless microphone 112 is not working, the system may activate an alarm module 157 which produces an audible alarm (e.g., via a speaker) in the OR 100 and/or a visual alarm or warning on the monitor 202. In some embodiments, the audible or visual alarm includes a voice instruction to the user (e.g., "check microphone"). In some embodiments, voice control is automatically re-enabled or reestablished when the microphone 112 re-enters the OR 100. In other embodiments, voice control must be explicitly reactivated.

The system may notify the user with the audible alarm and, in some embodiments, also correct a status misclassification. For example, if a user speaks softly, or if there is too much noise in the room, the reference microphone may not pick up enough of the voice signal, so that the CCRM algorithm may classify the state as out-of-room. The out-of-room classification is then announced by playing an audible alarm. However, if the wireless microphone is still in the room, the audible alarm will be picked up by the wireless microphone 112, allowing the algorithm to reverse the previous incorrect classification decision and the system to re-enable voice control.

In another embodiment, the detection module may take advantage of other audible signals present in the OR, as long as those audible signals contain enough information to discriminate among different ORs. For example, the human heart-beat pattern (rate, minor irregularities in the heart-beat rate or arrhythmia) differs from person to person. The sound of a heart-beat monitor can then be recorded at the first communication channel (i.e., wireless microphone) and compared with an electrical signal (e.g., analog or digital) representative of the heart-beat received from the heart-beat monitor itself. Information such as heart-beat rate, phase (between the two signals) and heart-beat-rate irregularities or arrhythmia (note that even healthy people will generally show some form of irregularity in their heart-beat rate) may then be used to compare the two signals and thus determine whether the wireless microphone is either inside or outside the desired OR. If the wireless microphone is in the desired OR, the heart-beat sound received at the first communication channel will have similar characteristics to the signal at the heart-beat monitor, and voice control would remain enabled. If the wireless microphone is in a different OR, the heart-beat sound would either be missing from the first communication channel, or have different characteristics from the heart-beat in the desired OR. The detection module may then disable voice control in the desired OR.

In another embodiment, in addition to the one or more reference microphones located in the OR, other reference microphones may also be located in one or more adjacent ORs. Performing CCRM analysis between the wireless microphone signal and the signals from the several reference microphones, the detection module may also rely on a positive confirmation indicating that the user is not in the correct OR. For example, with a first reference microphone placed in a first OR, when the user leaves the first OR and enters a second OR with a second reference microphone; any voice input received at the wireless microphone will show little similarity to the input at the first reference microphone in the first OR. However, there would be a high similarity to the input at the second reference microphone in the second OR. The detection module 152 would then disable the voice control in the first OR. Other reference microphones may be placed in areas of interest where it is desirable to detect the presence of the user, like for example near the OR door(s) (inside or outside), in hallways, scrub rooms, etc. Using more than one reference microphone may also reduce the margin of error of the detection module.

The detection module 152 may also be in communication with detection modules in other ORs. When either detection module determines that the wireless microphone has moved from a first OR to a second OR, the detection module in the second OR may instruct the detection module in the first OR to disable pairing of the wireless microphone in the first OR, and issue an optional audible signal and/or graphical representation and automatically "pair-up" the wireless microphone with the detection module in the second OR. Optionally, the automatic "pair-up" may be confirmed (e.g., the system asks "Do you want to use voice control in this OR?") prior to "pairing-up" the wireless microphone with the second detection module.

Figure 6:
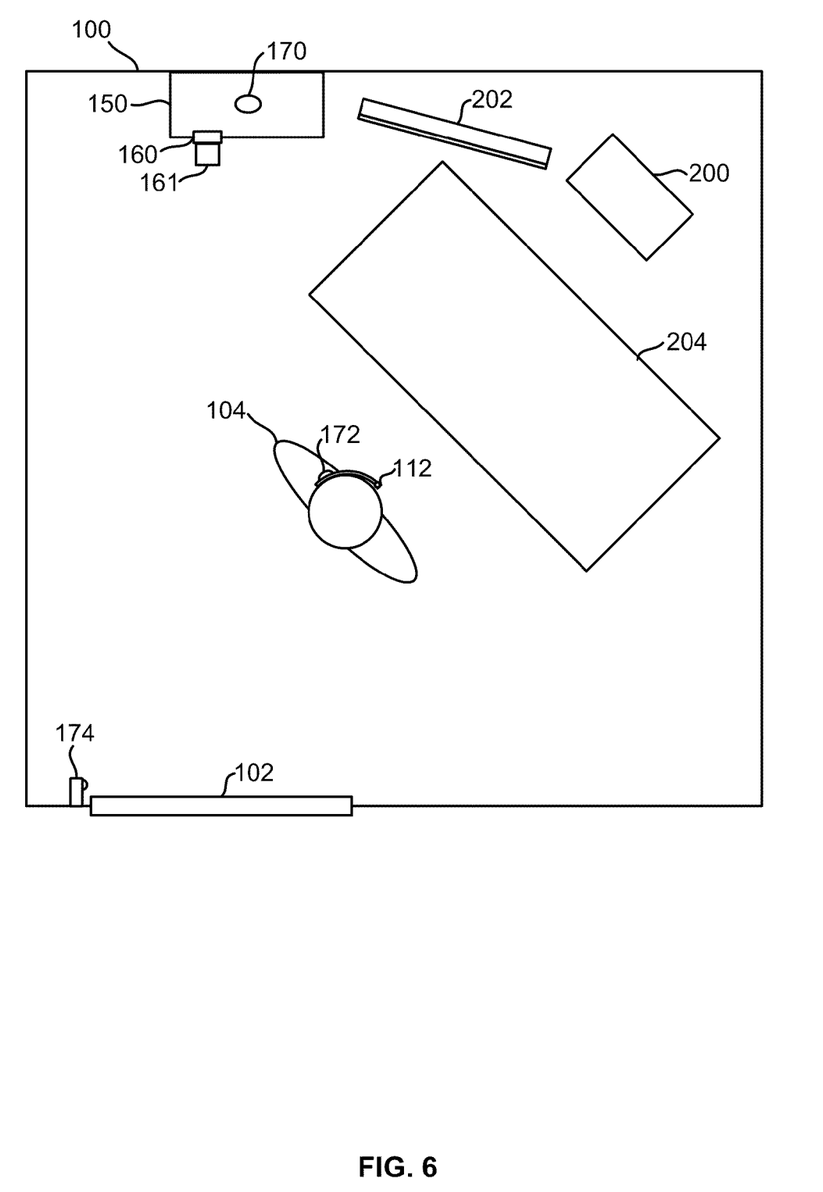
FIG. 6 is another top view of an operating room including a system according to an exemplary embodiment of the present invention.

FIG. 6 is another top view of an operating room including a system according to an exemplary embodiment of the present invention. In the exemplary embodiment, the system includes a reference communication device 170. The reference communication device 170 may be, for example, an ultrasound transmitter.

In the case of an ultrasound transmitter 170, sound is recorded via the wireless microphone 112 at a high sampling rate. The ultrasound transmitter 170 emits a signal having at least one frequency in the ultrasound frequency band (above 18 kHz). The wireless command microphone 112 is adapted to receive audio in the frequency bands associated with human speech and the ultrasound frequency bands. The user's speech and the ultrasound signal may be received by the wireless microphone 112. The detection module 152 (and/or other module) includes a filter that is applied to filter out the ultrasound frequency band from the audio signal that is used for voice control. If an ultrasound signal is detected, voice control is enabled. Ultrasound signals generally do not travel through walls, floors and ceilings easily. Thus, if an ultrasound signal is not detected, the wireless microphone 112 is out of the room, or there is a malfunction in the audio channel (e.g., dead battery, lost wireless communication link, etc.).

If an ultrasound signal is not detected, voice control is disabled. For example, the communication channel may be disabled at the microphone 112 or at the sound card 160. The voice control module 154 may also be prevented from issuing control data 140, e.g., by the switch module 156. The system may also activate an audible alarm in the OR 100 and/or a visual alarm or warning on the monitor 202. In some embodiments, the alarm includes a voice instruction to the user e.g., identifying the problem and/or instructing the user how to correct the problem.

In other embodiments, the ultrasound frequency is not filtered out by the detection module 152. The voice control module, e.g., including a speech recognition engine, is instead adapted to receive and process the ultrasound frequency, so that in the case where the ultrasound frequency is missing the voice command (or audio input) can be easily rejected or ignored. For example, the voice control module and/or speech recognition engine may be adapted to discriminate speech input from silence and/or background noise. The voice detection module can be further adapted to ignore any speech input unless the ultrasound frequency is present in the signal. As another example, the voice control module may include an acoustic model (e.g., based on HMMs, neural networks, or other suitable technologies) which is usually trained (e.g., by an offline process) on a large amount of speech data, preferably recorded in acoustic and environmental conditions that approximate those of the target use environment. If the acoustic model is trained on speech data that also include the ultrasound frequency, then the lack of such ultrasound frequency at recognition time would cause a poor match with the acoustic model and thus cause the recognition result to be rejected. Other means to prevent voice commands from being implemented when the ultrasound frequency is not recorded may also be employed.

In other embodiments, the reference communication device 170 is a receiver and/or transmitter, such as radio frequency identification ("RFID") receiver and/or transmitter. The wireless command microphone 112 may also include a tag 172 including information, such as an RFID tag containing a microchip and antenna in a compact package. The tag 172 receives signals from the reference communication device 170 and returns the signal. In some embodiments, the tag 172 returns the signal with additional data such as a unique identification number. However, a unique identification number is not required in all embodiments.

If an RFID tag is used, the particular tag is identified as being associated with a particular microphone. When the wireless command microphone having the particular tag identification is present in a particular OR, voice control in that OR is enabled. When it determined that the wireless command microphone 112 having the particular tag identification is outside of the OR 100, the system disables voice control. The system may also activate an audible alarm in the OR 100 and/or a visual alarm or warning on the monitor 202.

Radio-IR tags may also be used to determine if the microphone 112 is in the OR 100. In one embodiment, the OR 100 is illuminated with diffuse IR (e.g., modulated to identify the particular room) and detected at the microphone. For example, an RFID tag (e.g., on the wireless command microphone 112) with an IR signal detector may detect the IR signal and broadcast via radio both the RFID tag's ID and a room ID (decoded from the IR signal). The reference communication device 170 detects the broadcast and software executing on the computer 150 tracks/displays the tag's location to determine whether the tag is in the OR. Alternatively, the diffuse IR may be emitted from the wireless command microphone 112 (and/or its body pack) to station detectors in the OR, wired to the control computer 150.

In another embodiment, the system includes a detector 174 at the door 102 to detect when the tagged wireless command microphone 112 passes through the door 102 of the OR 100. The detector 174 may be a radio frequency monitor (e.g., 1.95 MHz, 3.25 MHz, 4.75 MHz or 8.2 MHz) for detecting the RFID tag 172. In other embodiments, the detector 174 may be a magnetic or magnetic-harmonic detector an acousto-magnetic or magnetostrictive monitor or a microwave monitor. In some embodiments, the detector 174 may determine the direction of transit (e.g., into the OR 100, or out of the OR 100).

The system may communicate to the control computer 150 to disable voice control. Voice control may automatically be reestablished when the wireless command microphone 112 re-enters the OR 100, or voice control may be explicitly re-enabled by the user or OR staff.

Figure 7:
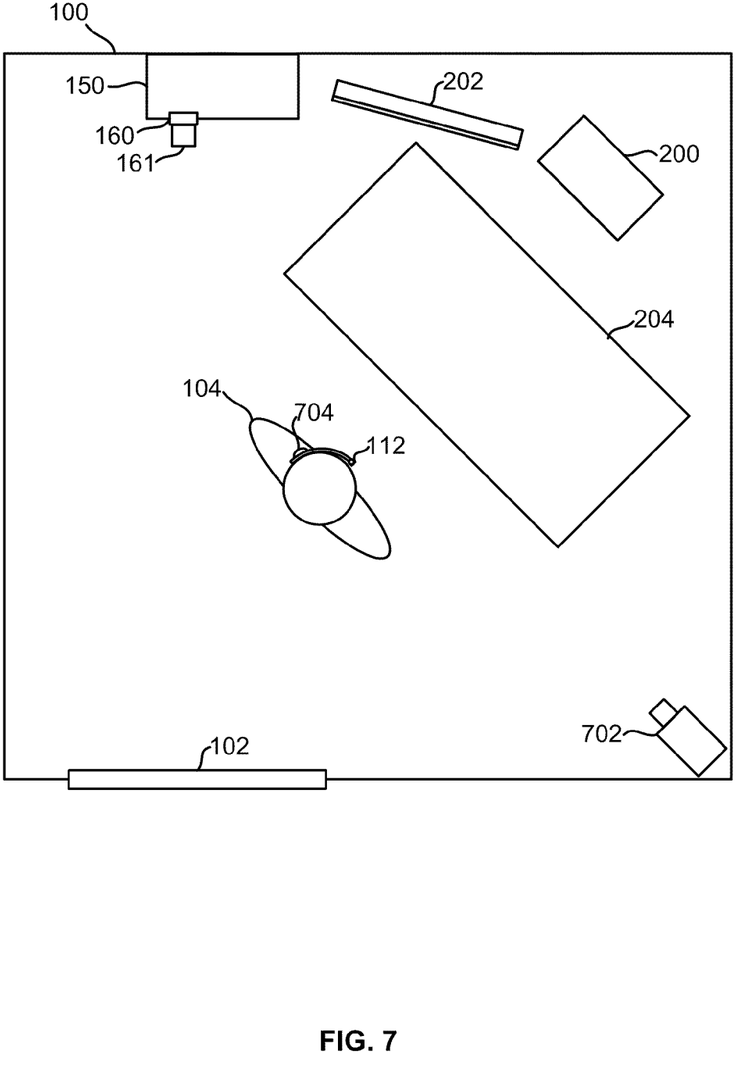
FIG. 7 is another top view of an operating room including a system according to an exemplary embodiment of the present invention.

In another embodiment, shown in FIG. 7, the detection module 152 includes or communicates with an image recognition module (e.g., in the computer 150) adapted to detect users wearing the wireless command microphone 112. At least one video camera 702 (or a plurality of video cameras) feeds a video signal to the image recognition module. The at least one video camera 702 may be adapted to scan the whole OR area and to communicate with the image recognition module. The image recognition module may instruct the video camera 702 to tilt and/or zoom-in on areas of interest where the presence of a wireless microphone 112 is suspected. Once the image recognition module positively identifies the presence of a wireless command microphone 112 in the OR, an audible and/or graphical message is generated to instruct the user of the wireless command microphone 112 to check-in with the system and for example execute a pairing-up procedure to assign the wireless command microphone 112 to operate with the wireless receiver in that OR. The pairing-up procedure is such that any previous pairing of the wireless command microphone 112 is broken before the new pairing is established.

The wireless command microphone 112 may include special visual features 704 (easily identifiable symbols or tags, IR emitters/reflectors, etc.) to ease the task and reliability of the image recognition module. The visual features 704 may also be used to uniquely identify each particular wireless command microphone 112. The detection module may also be in communication with detection modules in other ORs and dynamically break-up wireless pairings and establish new ones without any user intervention (besides an optional confirmation step). For example, the system may include a pairing manager module which maintains a list of existing associations (pairings) between wireless command microphones and ORs. As the system starts up (i.e., no pairing of any microphone to any OR), the detection of a certain wireless command microphone (e.g., visually identified by a tag representing the letter A) in a first OR will establish the pairing of wireless command microphone A with the first OR. A record indicating such association is added to the pairing manager module. If another wireless command microphone (B) is detected in the first OR, the detection module queries the pairing manager module to retrieve information about wireless command microphone B and the first OR. The pairing manager will indicate that wireless command microphone B is not paired to any OR, but that the first OR is already paired to wireless command microphone A. The detection module will decide then that wireless command microphone B must remain un-paired. If wireless command microphone A later moves to a second OR, the detection module in the second OR will query the pairing manager module. The pairing manager module will indicate that wireless command microphone A is already paired to the first OR. The detection module in the second OR will then instruct the detection module in the first OR to disable the pairing with wireless command microphone A (and/or to disable voice control in the first OR or the communication channel) and then update the information of the pairing manager module (pairing of A to first OR is removed from the list). If no other wireless command microphone is paired to the second OR (the result of another query to the pairing manager), the detection module in the second OR may then automatically (with optional user confirmation) pair-up wireless command microphone A with the wireless receiver in the second OR and inform the pairing manager of the new pairing (A to the second OR). In the case where more than one wireless command microphone is allowed to operate the voice control module in a particular OR, then the above rules can be extended to allow a second pairing for the OR (after disabling any pre-existing pairing of the second wireless command microphone).

Although the invention has been described with reference to a particular arrangement of parts, features and the like, these are not intended to exhaust all possible arrangements or features, and indeed many modifications and variations will be ascertainable to those of skill in the art.

What is claimed is:

1. A voice controlled surgical system, comprising:
   a wireless command microphone receiving audio input;
   a voice control module for generating commands from the audio input received by said wireless command microphone;
   a detection module for generating signals indicative of a proximity of said wireless command microphone;
   a switch module for disabling the commands in response to one or more of the signals; and
   an alarm module activated in response to the one or more of the signals.

2. The system according to claim 1, wherein the alarm module produces an audible alarm.

3. The system according to claim 2, wherein said switch re-enables the commands if the audible alarm is detected in the audio input by said detection module.

4. The system according to claim 2, wherein the audible alarm includes a voice instruction.

5. The system according to claim 1, wherein the alarm module produces a visual warning.

6. The system according to claim 1, further comprising:
   at least one video camera recording video images of an operating room; and
   an image recognition module, in communication with said detection module, receiving the video images and generating a signal indicative of the wireless command microphone being present in the operating room if the wireless command microphone is identified in the video images.

7. The system according to claim 6,
   wherein the wireless command microphone includes at least one visual feature uniquely identifying the wireless command microphone.

8. The system according to claim 1, further comprising:
   a receiver in an operating room;
   wherein the wireless command microphone is paired with said receiver upon determining that the wireless command microphone in the operating room.

9. The system according to claim 1, wherein said detection module generates a first signal when said wireless command microphone is outside of a particular room; and wherein said detection module generates a second signal when said wireless command microphone is inside the particular room.

10. The system according to claim 9, wherein said detection module generates a third signal in response to at least one of a power and communication loss with said wireless command microphone.

11. The system according to claim 1, wherein said wireless command microphone has a predetermined range, wherein said detection module generates a signal when the wireless command microphone is outside of the predetermined range.

12. The system according to claim 1, further comprising:
   a signal indicative of a heart rate received by said detection module, wherein said detection module compares the audio input received by said wireless command microphone and the signal indicative of the heart rate, whereby said switch module is responsive to said detection module for disabling said voice control module when the first audio input and the signal indicative of the heart rate are substantially different.

* * * * *